(12) United States Patent
Surwillo et al.

(10) Patent No.: US 6,915,155 B2
(45) Date of Patent: Jul. 5, 2005

(54) MEDICAL TESTING SYSTEM WITH AN ILLUMINATING COMPONENT AND AUTOMATIC SHUT-OFF

(75) Inventors: John M. Surwillo, Milwaukee, WI (US); Patricia J. Mikula, Thiensville, WI (US); Gary J. Secora, Brookfield, WI (US); Glenn N. Stern, Hartland, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 151 days.

(21) Appl. No.: 09/915,672

(22) Filed: Jul. 26, 2001

(65) Prior Publication Data

US 2003/0023174 A1 Jan. 30, 2003

(51) Int. Cl.[7] .............................................. A61B 5/0402
(52) U.S. Cl. ...................................... 600/509; 600/450
(58) Field of Search ................................. 600/300, 301, 600/384, 450, 483, 508, 509, 512, 516, 517, 520, 522, 523, 525, 437; 362/83, 85, 97–99

(56) References Cited

U.S. PATENT DOCUMENTS

| | | | | |
|---|---|---|---|---|
| 4,316,249 A | * | 2/1982 | Gallant et al. | 364/417 |
| 4,365,290 A | * | 12/1982 | Nelms et al. | 364/200 |
| 5,178,149 A | * | 1/1993 | Imburgia et al. | 600/463 |
| 5,474,090 A | * | 12/1995 | Begun et al. | 600/520 |
| 5,501,229 A | * | 3/1996 | Selker et al. | 128/696 |
| 5,590,648 A | | 1/1997 | Mitchell et al. | |
| 5,649,544 A | | 7/1997 | Feng | |
| 5,687,717 A | | 11/1997 | Halpern et al. | |
| 5,833,623 A | | 11/1998 | Mann et al. | |
| 5,868,487 A | * | 2/1999 | Polley et al. | 362/33 |
| 6,149,587 A | * | 11/2000 | Raines | 600/300 |
| 6,380,921 B2 | * | 4/2002 | Nakamura | 345/102 |
| 6,506,155 B2 | * | 1/2003 | Sluis | 600/437 |

OTHER PUBLICATIONS

*Case® 8000 Cardiac Assessment System*, Feb. 1999.
Virtual Hospital informational pages entitled *Virtual Hospital: Iowa Health Book: Internal Medicine, Treadmill Electrocardiogram (Stress EKG)*, Jun. 25, 2001.
New York University, Hippocrates Project NYU School of Medicine, entitled *EKG Tutorial Part I*, printed Jun. 25, 2001 (copyright 1992–1997).
Marshall Brain's *How Stuff Works—How Heart Attacks and Angina Work*, printed Jun. 25, 2001.
WebMDHealth, Medical Library, *Test Name—Electrocardiogram*, printed Jun. 25, 2001.

* cited by examiner

Primary Examiner—Jeffrey R. Jastrzab
Assistant Examiner—Frances P. Oropeza
(74) Attorney, Agent, or Firm—Andrus, Sceales, Starke & Sawall, LLP

(57) ABSTRACT

A medical testing system has an instrument for monitoring a characteristic of a patient and an illuminating component for illuminating the instrument. The instrument includes a component for selectively activating and deactivating the illuminating component and a deactivating component for automatically deactivating the illuminating component, after a predetermined period of time has elapsed.

6 Claims, 6 Drawing Sheets

MEDICAL TESTING SYSTEM WITH AN ILLUMINATING COMPONENT AND AUTOMATIC SHUT-OFF

BACKGROUND OF THE INVENTION

The field of the invention generally relates to a medical testing system, and more particularly, to a medical testing system with an illuminating component.

Heart disease is the leading cause of death in the U.S. Heart disease is any condition that causes your heart to malfunction. When the words "heart disease" are used generically, it usually refers to coronary heart disease which leads to heart attacks and angina, ultimately caused by atherosclerosis. But there are a wide range of other diseases of the heart such as congestive heart failure, valvular heart disease, diseases of the heart valves, cardiac arrhythmias, i.e., irregular heartbeats, diseases of the pericardium (sac around the heart), diseases of the myocardium (heart muscle), endocarditis (infection of a heart valve), and congenital heart disease, i.e., birth defects of the heart. There are a number of tools that are available to a physician to help monitor and diagnose malfunctions of the heart. They include history and physical examinations, chest x-ray, blood tests, echocardiograms, cardiac catheterizations, electrocardiograms, and EKG stress tests.

An electrocardiogram ("EKG" or "ECG") for example records the electrical activity of the heart at rest. For an EKG measurement, electrodes are usually placed on the arms, legs and chest of a patient. These electrodes are connected by wires to an EKG machine. A twelve lead EKG is typically used which generates twelve different tracings or waveforms. Each waveform provides a view of the heart from a different angle. These waveforms are stored in memory and if a monitor is used, the waveforms are displayed. In addition, the waveforms may be recorded on paper by a thermal writer or any other conventional writer. A paper roller is driven by a motor that feeds the paper across a heated printer head. The physician may view and analyze the waveforms on the paper which moves across a work surface of the EKG machine. A physician may be able to determine the location of a heart attack based on the EKG lead involved. Then, based on his/her knowledge of anatomy, the physician may be able to determine which artery is blocked. The EKG gives the physician information about heart rate and rhythm, heart blood supply sufficiency, heart attack, heart enlargement, inflammation around the heart, drug effects, and electrolytes on the heart.

An EKG stress test is another commonly used procedure to evaluate coronary artery disease. It uses a similar EKG machine as described above with electrodes appropriately positioned on a patient to measure the electrical activity of the heart. However, these measurements are taken when the heart is exercised, i.e., "under stress." EKG stress tests are useful because exercise can reveal abnormalities that were not detected during an EKG of the heart at rest. In this procedure, a person's EKG is initially monitored at rest and then monitored while walking on a treadmill or pedaling a bicycle. The exercise is gradually increased until a target heart rate is reached. If severe EKG changes, chest pain, severe shortness of breath, blood pressure changes or cardiac arrhythmias occur, then the physician may stop the stress test. The EKG stress test may uncover problems with the heart rhythm or blood supply to the heart or may provide valuable planning cardiac rehabilitation after a heart attack or heart surgery.

An echocardiogram ("echo") is yet another commonly used procedure to evaluate coronary heart disease. The echo uses an ultrasonic beam to view the heart in motion. In this procedure, an ultrasonic transducer, similar in appearance to a microphone, transmits and receives ultrasonic waves. The transducer is placed on the chest wall and maneuvered to view different portions of the heart on a monitor. In order to best view the monitor, stress echo tests are performed with the room lights dimmed and the sunlight suppressed. The echo is used to evaluate the presence of several abnormalities of the heart including (1) abnormal fluid collection in the pericardium, (2) valve obstruction or leaks, (3) chamber size, thickness of heart wall, as well as other problems.

In some instances, the EKG and echo stress test procedures are conducted separately at different locations. There is, however, a growing trend among hospitals and health care providers to use an EKG stress testing system in conjunction with an echo stress testing system at the same location. In a typical evaluation at a stress laboratory, a patient would first undergo an EKG stress test. Immediately following, usually within 10 seconds, but before the patient's heart returns to normal, the patient would quickly move to a resting bed to receive an echo stress test by an echo technician. During this time, the physician continues to evaluate the EKG waveforms which appear on the paper along the work surface of the EKG machine. Because an echo stress procedure is usually performed in the darkness, the physician is unable to view, analyze and make appropriate notes on the paper relative to the waveforms with the signals received from the electrodes. If or when the physician is able to complete his analysis of the EKG waveforms, he/she is unable to manipulate the keypads to turn the thermal writer off or control any of the other functions of the EKG machine. In sum, the physician is severely disadvantaged because of the darkness.

SUMMARY OF THE INVENTION

In an exemplary embodiment of the invention, a medical testing system comprising an instrument for monitoring a characteristic of a patient; and an illuminating component for illuminating the instrument, the instrument including: a component for selectively activating and deactivating the illuminating component; and a deactivating component for automatically deactivating the illuminating component, after a predetermined period of time has elapsed.

In another exemplary embodiment of the invention, a medical testing method comprising the steps of: activating an illuminating component positioned relative to an instrument for monitoring a characteristic of a patient, the instrument including a keypad having a plurality of keys; determining if a key on the plurality of keys has been pressed by a user; and automatically deactivating the illuminating component if a key of the plurality of keys has not been pressed within a predetermined period of time.

In yet another exemplary embodiment of the invention, a medical testing system comprising: an instrument for monitoring the electrical activity of a patient's heart; an illuminating component for illuminating the instrument; the instrument including: a component for selectively turning the illuminating component on and off; a component for automatically turning the illuminating component off, after a predetermined period of time has elapsed.

In yet another exemplary embodiment of the invention, a computer program for performing a method comprising the steps of: activating an illuminating component positioned relative to an instrument for monitoring a characteristic of a patient, the instrument including a keypad having a plurality of keys; determining if a key on the plurality of keys has been pressed by a user; and automatically deactivating the illuminating component if a key of the plurality of keys has not been pressed within a predetermined period of time.

In another exemplary embodiment of the invention, a medical testing system comprising: means for monitoring the electrical activity of a patient's heart; means for illuminating the instrument, the instrument including: means for selectively turning the illuminating component on and off; and means for automatically turning the illuminating component off, after a predetermined period of time has elapsed.

DESCRIPTION OF THE PREFERRED EMBODIMENT

Figure 1:
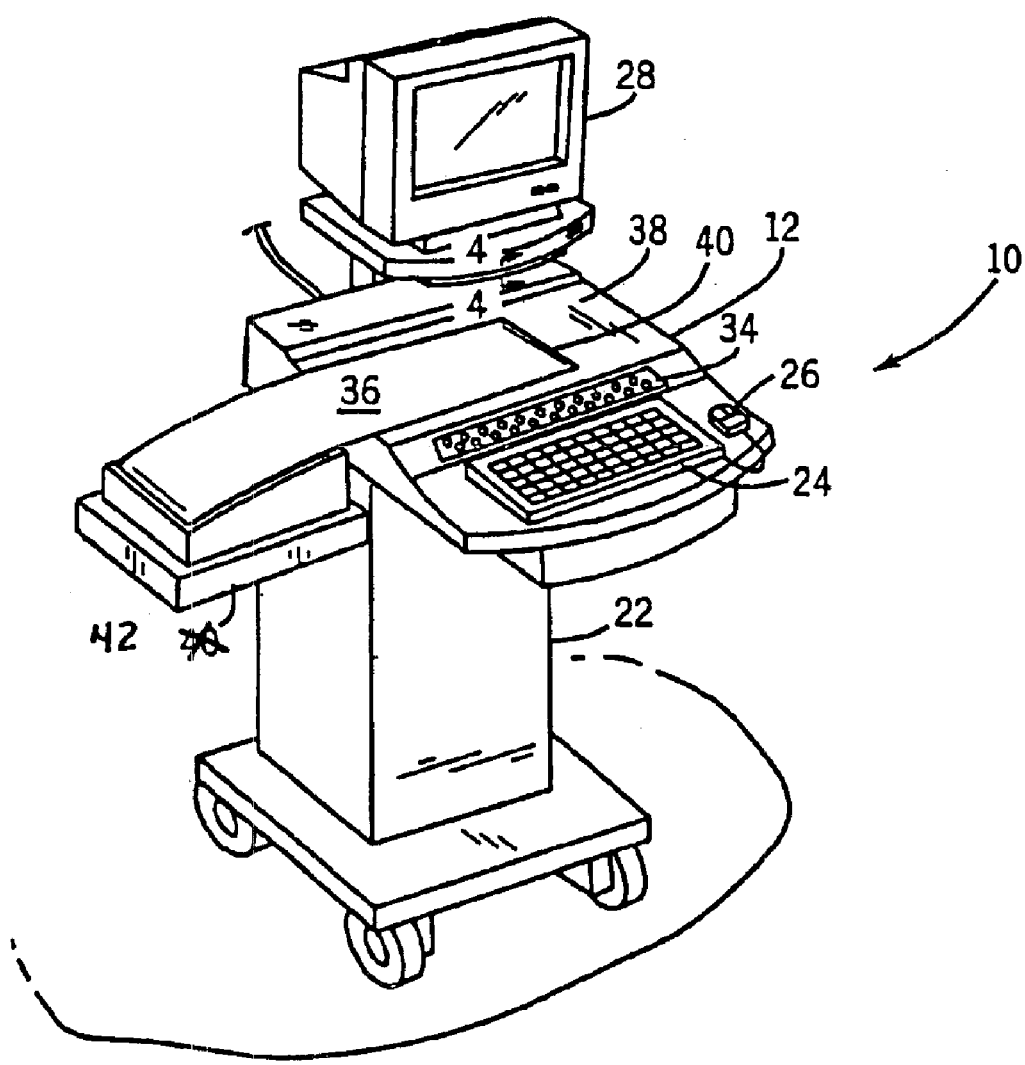
FIG. 1 is a perspective view of the EKG stress testing system which employs a preferred embodiment of the present invention.
Figure 2:
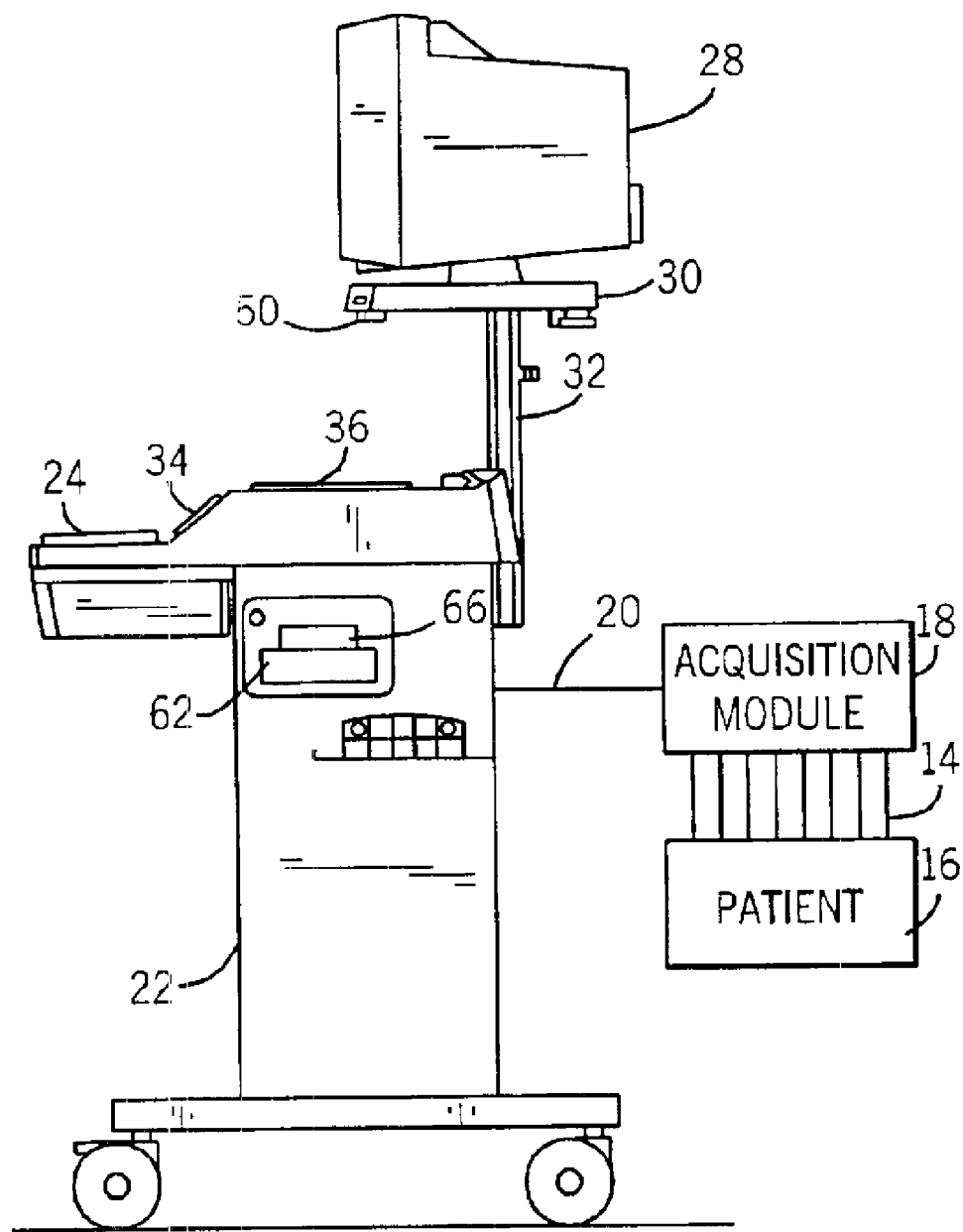
FIG. 2 is a side view of the EKG stress testing system shown in FIG. 1.

Referring to FIGS. 1 and 2, there is shown an EKG stress testing system 10 which incorporates a preferred embodiment of the present invention. System 10 includes instrument 12 for controlling the entire operation of system 10, including processing function commands and the signals generated from a plurality of electrodes 14 attached to a patient 16. Each electrode has a corresponding wire of preferably two feet length. In this embodiment, electrodes 14 are coupled to instrument 12 by way of a cardiology acquisition module 18 and central cable 20. Cable 20 (preferably 20 feet) connects acquisition module 18 to instrument 12 and preferably has a connector with 10–12 pins and locking tabs to ensure that the user properly connects cable 20 to the appropriate port on an acquisition card (discussed below) in the rear of instrument 12 and that cable 20 does not become disconnected during testing. The ports in the rear of instrument 12 are accessible through a large opening which is exposed when a flap down door is opened with a tool (not shown). Acquisition module 18 functions to convert the analog signal generated from electrodes 14 into digital signals for instrument 12. This is accomplished by several known components including a digital to analog converter. Acquisition module 18 also includes protection circuitry to protect instrument 12 from receiving high energy jolts from a defibrillator.

Instrument 12 is mounted in a movable cart 22 for maneuverability and for transporting system 10 from one location to another. System 10 includes several operator control devices, similar to that used in for a personal computer, such as keyboard 24, mouse 26 and monitor 28. These devices are coupled or connected to the instrument 12 via conventional communication ports that appear in the rear of a computer (video, PS/2, com1), as discussed above. In the present preferred embodiment, keyboard 24 and mouse 26 are conventional components which can be purchased off the shelf. Monitor 28 may also be purchased off the shelf. The presently preferred embodiment includes particular component circuitry to isolate a monitor's high voltage requirements from a patient to satisfy UL and other power limitation requirements. The isolation circuitry will be discussed in more detail below.

Monitor 28 is supported by plate 30. Neck 32 is attached underneath to plate 30 and to the rear of instrument 12. Several screws and bolts (six) are used to fasten plate 30 to a flat portion of neck 32 through corresponding holes in each. The plate 30 and neck 32 function together to support and position monitor 28 above instrument 12. In the present preferred embodiment, the height of monitor 28 is fixed relative to instrument 12. Neck 32 is fastened to a bracket in the rear of instrument 12 using nuts which are screwed onto threaded studs on neck 32. However, in other embodiments, the neck or other structure may be designed for adjustment to enable plate 30 to pivot or rotate horizontally with respect to instrument 12. In addition, the monitor support structure may be adapted to attach to other surfaces such as a table or desk.

Instrument 12 also includes a dedicated keypad 34 which includes an elastomer pad, key bezel with keys and printed circuit board combined. In operation, the keys press on the elastomer which has conductive pills that press down on the printed circuit board and close a circuit of copper traces on the printed circuit board. Keypad 34 refers to these components as combined. The keys of keypad 34 are located above the area for keyboard 24. Keypad 34 is used to control the treadmill and stress test specific functions. For example, there are preferably keys to control the treadmill such as start/stop, speed and incline keys. There are preferably keys relating to the instructions for the testing part of the procedure (testing phase settings) such as new test, pretest, exercise, recovery, test end, hold/pause, and blood pressure entry. These keys may require personal data input via keyboard 24. In addition, there are preferably keys relating to report generation and control such as start and stop thermal writer.

In the preferred embodiment, there are 22 keys in total, each with a backlight to illuminate the key itself. However, any number of keys may be employed. One key is used to toggle (turn on and off) the light source (illuminating component, discussed below) as well as the backlights for the keys themselves. The remaining 21 keys are keys to enable function of the system 10, as discussed above.

As will be discussed in more detail below, instrument 12 (internally) includes a thermal writer in which a paper roller is driven by a motor that feeds paper 36 across a heated printer head. Instrument 12 also includes work surface 38 over which paper record 36 extends. Waveforms generated from electrodes 14 are recorded and printed on paper 36 as it moves through a slot 40 in work surface 38. As paper 36 moves across work surface 38, paper 36 accumulates in a bin 42 attached to moveable cart 22, located adjacent instrument 12.

Figure 3:
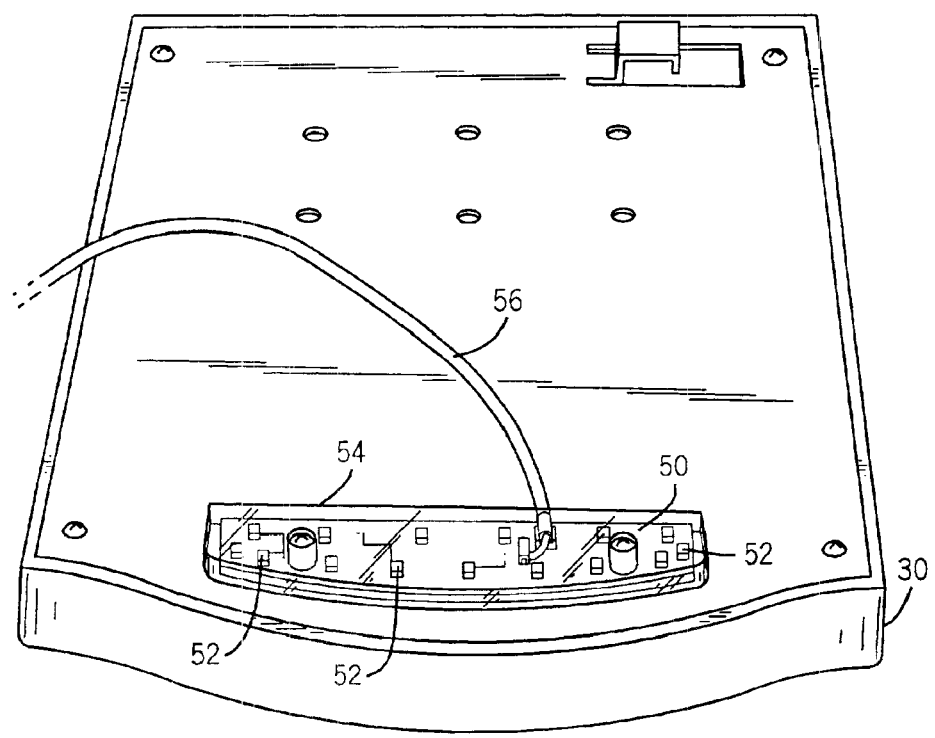
FIG. 3 is an LED circuit board attached to the bottom of the monitor plate for supporting the monitor shown in FIG. 1.
Figure 4:
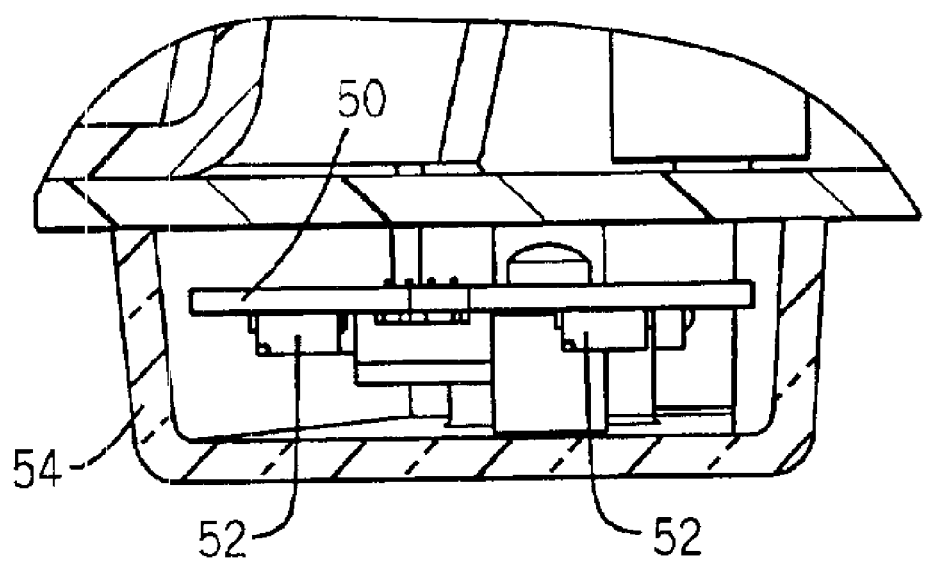
FIG. 4 is a cross-sectional view of the LED circuit board along lines 4—4 shown in FIG. 3.

Referring to FIGS. 2 and 3, system 10 also includes an illuminating component (light source) for illuminating work surface 38 and keypad 34. The illuminating component is a circuit board 50 which includes a plurality of light emitting diodes ("LED") 52. Circuit board 50 is covered by a clear plastic shield 54 which is bolted to and supported by the bottom front end of support plate 30. The LEDs 52 are positioned throughout circuit board 50. Preferably, 15 white LEDs are used. The position of the circuit board 50, together with the number and position of LEDs on circuit board 50 satisfy the following preferred light criteria: (1) the light is properly diffused; (2) minimal glare is produced on paper 36; and (3) the light will last a long time.

Note that the illuminating component preferably illuminates at least three areas or "zones." These zones are work surface 38, keypad 34, located just below work surface 38, and keyboard 24. This enables the physician to read and analyze the waveforms on paper 36 (on work surface 38) as well as view and manipulate the keys on keypad 34 and keyboard 24. System 10 includes cable 56 which is used to provide power to LED board 50 and LEDs 52 on board 50. Cable 56 has a connector which is adapted to connect to a port in the interior of instrument 12. It is important to note that the illuminating component may be of any type and may be positioned anywhere so long as the illuminating component illuminates at least the area in which a physician works on instrument 12.

Figure 5:
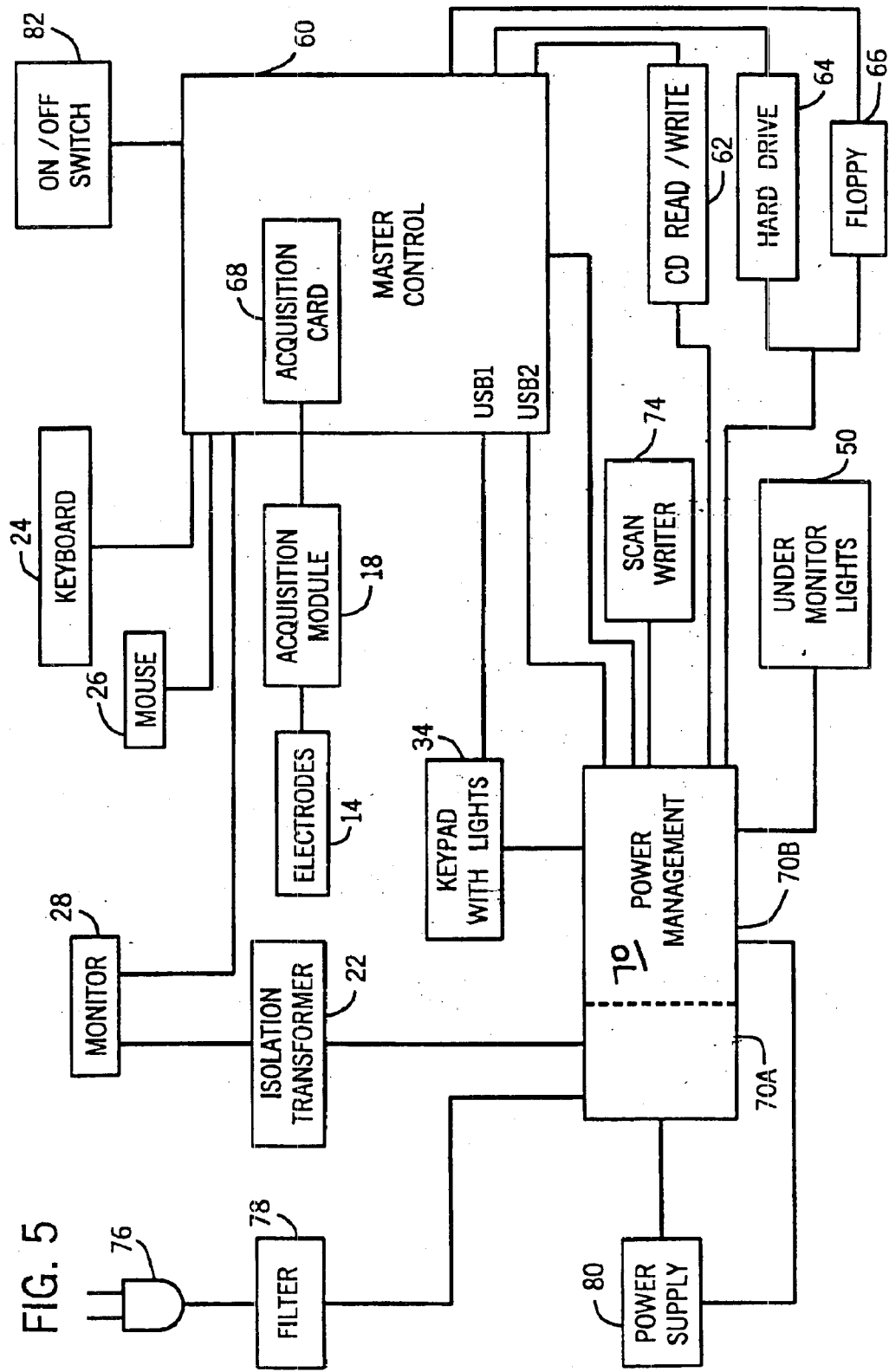
FIG. 5 is a block diagram of the components of the EKG stress testing system shown in FIG. 1.

Referring to FIG. 5, there is shown a block diagram representing the components of system 10. System 10 includes the customary components of a computer such as a master control or motherboard 60, a CD Read/Write drive 62, hard drive 64 and floppy drive 66. Master control 60 is used to control the high level operation of system 10. Master control 60 includes the customary components of a computer, such as a microprocessor (CPU), memory (RAM and ROM), and I/O devices. In the preferred embodiment, the motherboard includes a 566 MHz Intel Celeron microprocessor, 64 MB SDRAM and Windows NT.

Acquisition card 68 is inserted into a conventional slot on motherboard 60. Acquisition card 68 is used to provide a port for receiving cable 20 and additional ports for other peripheral devices (e.g., treadmill wires, automatic blood pressure devices, pulse oximeters). Acquisition module 18 is coupled to acquisition card 68 and electrodes 14 are coupled to acquisition module 18. In operation, patient 16 carries acquisition module 18 on his/her waist by a belt. Each electrode is attached to patient 16 at different points on his/her body. For most patients 16, electrodes 14 are preferably attached with "stick on contacts" that a technician sticks to the patient's shaven skin. In another embodiment, electrodes 14 may be attached to a patient using suction elements that run off a pump. The instrument 12 preferably includes a pump so the user has the option to choose either embodiment. In either embodiment, electrodes 14 are placed on the body in the traditional 12-lead electrode placement, which is a specific pattern across the chest and on all 4 limbs. Importantly, electrodes 14 generate analog signals which are converted by acquisition module 18 into digital signals for acquisition card 68.

As briefly indicated above, a conventional keyboard 24 and mouse 26 are connected to motherboard 60 at the appropriate conventional communication ports. In addition, monitor 28 is connected to a conventional video port on motherboard 60. Instrument 12 includes a power management circuit board 70 for providing power to many of the components in instrument 12, including monitor 28. Also briefly discussed above, when designing and using medical equipment, it is important to isolate the power from the patient, particularly power at high levels, to prevent injury to the patient in all circumstances. In a typical medical environment, a special monitor with protection circuitry would be required to satisfy this function. In the present preferred embodiment, however, instrument 12 utilizes a separate protection device or isolation transformer 22 to isolate the power supplied to the monitor from patient 16. Thus, one may use any off the shelf monitor for this system.

In practice, monitor 28 is used to display many characteristics of the patient and of the procedure including the EKG instrument settings, the treadmill settings, e.g., grade, speed, blood pressure entered, number of leads, etc.

Power management board 70 is also coupled to motherboard 60, keypad 34, scan or thermal writer 74, CD Read/Write drive 62, hard drive 64, floppy drive 66, the under the monitor lights or circuit board 50 (illuminating component). (The scan writer includes a print head, a motor, paper roller and other components necessary for the operation of the scan writer). Power management board 70 has two portions 70A, 70B, which in the preferred embodiment, are integrated on the same board. However, these portions may be two separate boards.

Portion 70A is used to receive electricity from a wall socket via plug 76. Filter 78 is used to filter transient AC signals from the wall. Power is received and processed by portion 70A and fed to power supply 80. Power supply 80 is preferably two separate conventional medical grade power supplies. However, one would suffice. Power supply 80 is used to convert the power signal from the wall into appropriate DC signals for portion 70B of power management board 70. Portion 70B is used to supply such DC voltage signals to many of the components as seen in FIG. 5. Note that keypad 34 is shown connected to motherboard 60. Motherboard 60 provides a 5 volt supply to keypad 34 which is usually insufficient to independently power the 22 LEDs that are used to backlight each of the 22 LEDs on keypad 34. Therefore, keypad 34 is also coupled to power management 70 to receive adequate voltage (12 volts) to provide adequate current to drive the LEDs.

The circuit board of keypad 34 includes memory, a microcontroller unit and software to control the functions associated with the keys. The microcontroller may be of any type but preferably is a Cypress semiconductor (No. CY7C63101A-SC). There are preferably 22 keys in total. Twenty (21) are keys associated with the functions of the EKG instrument 12 or the treadmill ("function keys") and one key is associated with the lights ("light key"). If a user presses a function key, the software senses, interprets and decodes the signal as a particular command, and sends the command to motherboard 60 to implement the command. If a user presses the key to turn on the thermal printer, for example, the software interprets this signal and sends a command to motherboard 60. Motherboard 60 thereafter transmits a signal to power management board 70 to provide power to scan writer 74. (Specifically, a mosfet transistor on management board 70 receives the signal from motherboard 60 and turns on power to scan writer 74.) Note ON/OFF switch 82 activates the entire system 10.

A similar operation for execution occurs for all of the function keys. However, the operation of the light key is different. The operation is discussed in more detail below with reference to FIG. 6. In brief, however, the lights will toggle, i.e, turn on and off, in response to the depression of the light key. If the lights are off and the light key is pressed for example, the software senses this signal and sends a command directly to power management board 70 to turn all lights on, including the 15 LEDs under the monitor and the 22 backlights LEDs for each key. Note that in the preferred embodiment, the microprocessor on motherboard 60 is isolated or unaware of the operation of the lights.

The software on board of the keypad 34 also has another feature relating to the lights. This feature is known as automatic light shut off. If the lights remain on for a predetermined period of time without any activity from the user, the software will automatically turn the lights off. The predetermined period is preferably set to an hour but any desired length may be set. This automatic shut off feature improves or increases the life of all LEDs. (light intensity of LED's gradually to dim over time.) The operation of the software with respect to the lights is discussed below.

Figure 6:
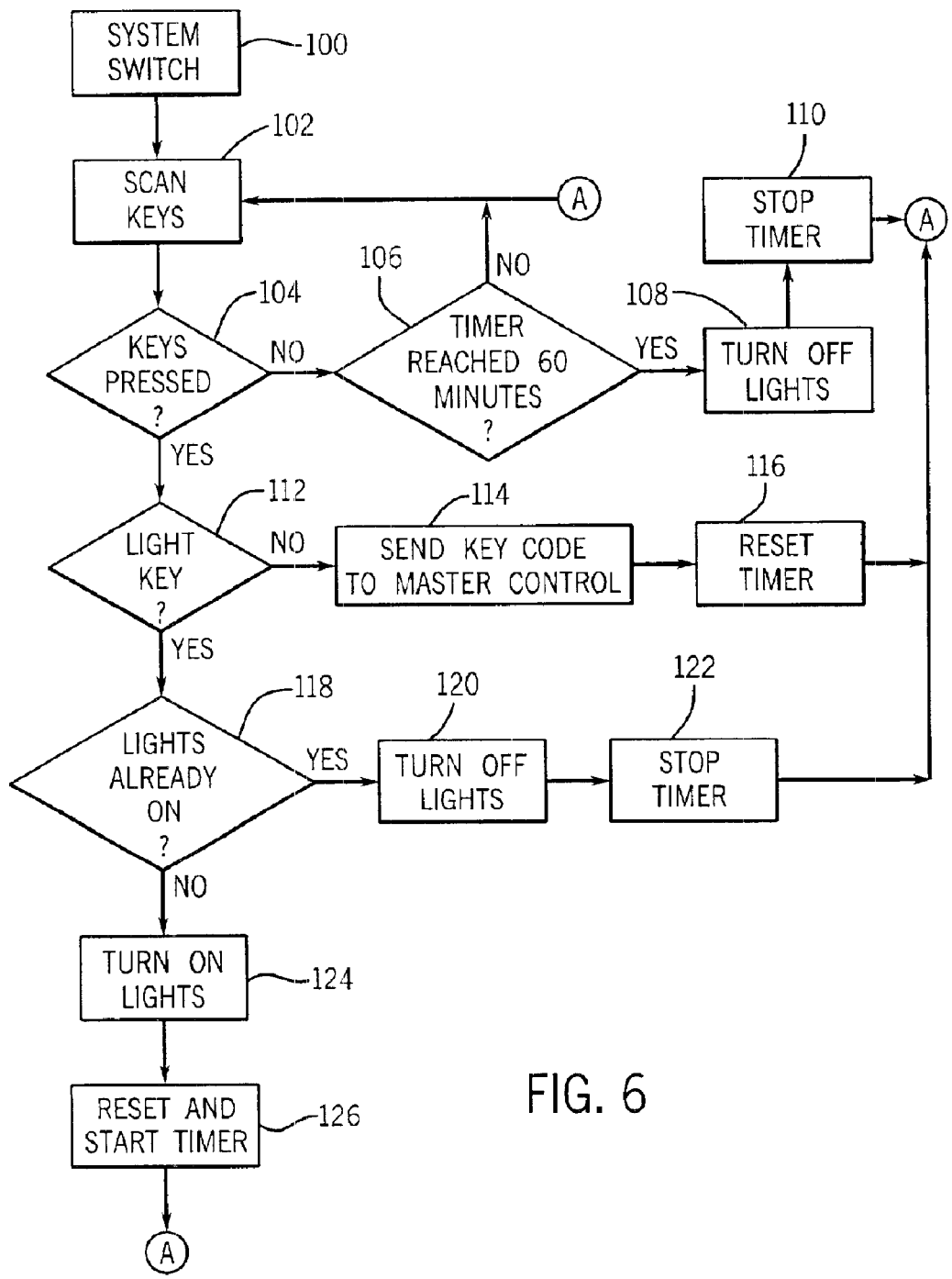
FIG. 6 is a flowchart of the program for the implementation for automatic shut off for the LEDs.

Referring to FIG. 6, there is shown a flowchart for the software for the keypad 34 illustrating the execution steps of the method for implementing automatic light shut-off. As a first step 100, a user flips a switch and turns on the entire system 10. For purposes of the flowchart, the lights are presumed to be off for the initial settings status.

Now, execution proceeds to step 102 wherein the keys of the keypad 34 are scanned for a signal associated with a key depression. The scanning is performed by a matrix configuration. (Keypad 34 has 22 keys, where 21 are in a 3 by 8 matrix. Note that the light key, i.e., the $22^{nd}$ key is routed directly into an input/output line on the microcontroller unit for light control. The 3 columns are outputs from the microcontroller on keypad 34, and the 8 rows are inputs to the microcontroller. During non-scanning, the 3 columns are all sitting at logic high, and the 8 rows all have internal pull-up resistors that make those lines logic high, when the line is not being driven by a key press. During scanning, a column is set to logic low, and the 8 rows are checked to determine if any of those rows are set to a logic low at that time. If one row is detected, then it is known the key that is responsible for passing the logic low from that column to that row. The scan is continued for all 3 columns.) As long as the system 10 is activated, scanning is performed continually.

Execution then proceeds to decision box 104, wherein it is determined whether a user has pressed a key on keypad 34. If a key has not been pressed, then execution proceeds to decision box 106 wherein it is determined if the timer has reached 60 minutes. If 60 has been reached, then execution proceeds to boxes 108 and 110 wherein the lights are turned off and the timer is stopped. Then execution returns to box 102 wherein scanning continues. If the timer has not reached 60 minutes, execution returns to box 102 again. Because the presumption is the lights are not activated or on for the initial configuration, the software returns to scanning regardless of whether the timer is activated or has reached 60 minutes. Note that the timer function is preferably performed by a sub-routine of the software (on keypad 34) which is activated or updated by a hardware generated interrupt service routine on the microcontroller. However, the timer function may be achieved through a hardware timer.

Returning to decision box 104, wherein it is determined if a key on keypad 34 has been pressed. If the answer is YES, then execution proceeds to decision box 112, wherein the software determines if the key pressed or activated is the light key. If the answer is NO, the execution proceeds to box 114, wherein the software determines that the key activated is a function key and interprets and transmits the appropriate code or instruction to master control or motherboard 60 to implement the instruction for that function key. Following the transmission, execution proceeds to box 116 wherein the timer is reset. Execution then returns to scanning in box 102.

Now, if the answer to decision box 112 is YES, i.e., a user has pressed the light key, then execution proceeds to decision box 118, wherein the software determines if the lights are already on (all LEDs). If the answer is a YES, execution proceeds to boxes 120 and 122 wherein the lights are turned off (all 37 LEDs) and the timer is stopped. Following this, execution returns to scanning in box 102. If the answer to decision box 118 is NO, then execution proceeds to box 124 wherein the lights under the monitor (LEDs) and the backlights for the keys are turned on or activated. Following box 124, execution proceeds to box 126 wherein the timer is reset and the timer is started. Execution then returns to scanning in box 102. The flowchart described above is the preferred method of implementing light activation and automatic shut-off. There are, however, many other ways to achieve the same goals.

The foregoing description of a preferred embodiment of the invention has been presented for purposes of illustration and description. It is not intended to be exhaustive or to limit the invention to the precise form disclosed and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and their equivalents.

What is claimed is:

1. A medical testing system for monitoring the electrical activity of a patient's heart by successively performing both electrocardiogram and echocardiogram monitoring procedures in the same location, the system comprising:

a movable cart housing a central control system for controlling both the electrocardiogram and echocardiogram procedures;

the central control system comprising a display for displaying monitoring output from the electrocardiogram and/or echocardiogram monitoring procedures, a printer for printing monitoring output from the electrocardiogram and/or echocardiogram monitoring procedures, a work surface upon which the printed monitoring output is disposed, a keypad comprising a plurality of keys for inputting control commands to the control system to conduct the echocardiogram procedures, and a keyboard comprising a plurality of keys for inputting commands to the control system to conduct the electrocardiogram and/or echocardiogram procedures; and an illuminating component for selectively illuminating the work surface, keypad and keyboard and thereby facilitating successive performance of the electrocardiogram and echocardiogram monitoring procedures by allowing a caregiver to view and manipulate the keys on the keypad and keyboard and view the printed monitoring output regardless of surrounding lighting conditions of the location, wherein the illuminating component is automatically de-activated if a key on the keypad is not actuated for a predetermined time period.

2. The medical testing system of claim 1, wherein the movable cart comprises a plate for supporting the display above the work surface and the illuminating component is attached to the plate.

3. The medical testing system of claim 2, wherein the illuminating component comprises a circuit board having a plurality of light emitting diodes.

4. The medical testing system of claim 1, wherein the illuminating component comprises a circuit board having a plurality of light emitting diodes.

5. The medical testing system of claim 1, wherein the illuminative component can be activated or de-activated by actuating a key on the keypad.

6. The medical testing system of claim 1, wherein the illuminating component comprises a plurality of light emitting diodes.

* * * * *